United States Patent [19]

Dory

[11] Patent Number: 5,080,102

[45] Date of Patent: Jan. 14, 1992

[54] EXAMINING, LOCALIZING AND TREATMENT WITH ULTRASOUND

[75] Inventor: Jacques Dory, Coupvray-Esblay, France

[73] Assignee: EDAP International, S.A., France

[21] Appl. No.: 350,038

[22] Filed: Apr. 21, 1989

Related U.S. Application Data

[60] Division of Ser. No. 37,369, Apr. 13, 1987, abandoned, which is a division of Ser. No. 728,905, Apr. 30, 1985, Pat. No. 4,658,828, continuation-in-part of Ser. No. 674,889, Nov. 26, 1984, Pat. No. 4,617,931.

[30] Foreign Application Priority Data

Dec. 14, 1983 [FR] France ............................. 8320041
May 3, 1984 [FR] France ............................. 8406877

[51] Int. Cl.$^5$ .......................... A61B 8/00; A61N 5/00
[52] U.S. Cl. ............................... 128/660.03; 128/399
[58] Field of Search ............. 128/660.03, 244 A, 399, 128/804

[56] References Cited

U.S. PATENT DOCUMENTS 3,338,235  8/1967  Gordon .

(List continued on next page.)

FOREIGN PATENT DOCUMENTS

| 0036353 | 9/1981 | European Pat. Off. . |
|---|---|---|
| 0045265 | 2/1982 | European Pat. Off. . |
| 0090138 | 10/1983 | European Pat. Off. . |
| 0108190 | 5/1984 | European Pat. Off. . |
| 0124686 | 11/1984 | European Pat. Off. . |
| 0133946 | 3/1985 | European Pat. Off. . |
| 654673 | 12/1937 | Fed. Rep. of Germany . |
| 2053892 | 5/1972 | Fed. Rep. of Germany . |
| 2223319 | 12/1972 | Fed. Rep. of Germany . |
| 2202989 | 7/1973 | Fed. Rep. of Germany . |
| 2351247 | 4/1975 | Fed. Rep. of Germany . |
| 2645738 | 4/1977 | Fed. Rep. of Germany . |
| 2722252 | 11/1978 | Fed. Rep. of Germany . |
| 2913251 | 10/1980 | Fed. Rep. of Germany . |
| 2921444 | 11/1980 | Fed. Rep. of Germany . |
| 3119295 | 12/1982 | Fed. Rep. of Germany . |
| 3122056 | 12/1982 | Fed. Rep. of Germany . |
| 3142639 | 5/1983 | Fed. Rep. of Germany . |
| 3150513 | 6/1983 | Fed. Rep. of Germany . |
| 3210919 | 10/1983 | Fed. Rep. of Germany . |
| 3241026 | 5/1984 | Fed. Rep. of Germany . |
| 3316837 | 11/1984 | Fed. Rep. of Germany . |
| 3319871 | 12/1984 | Fed. Rep. of Germany . |
| 3328068 | 2/1985 | Fed. Rep. of Germany . |
| 3426398 | 3/1986 | Fed. Rep. of Germany . |
| 2247195 | 5/1975 | France . |
| 2477723 | 9/1981 | France . |
| 0487664 | 2/1982 | France . |
| 2487665 | 2/1982 | France . |
| 2546737 | 12/1984 | France . |
| 3589715 | 5/1987 | France . |
| 8400504 | 9/1985 | Netherlands . |
| 602180 | 4/1978 | U.S.S.R. . |
| 2113099 | 8/1983 | United Kingdom . |
| 2140693 | 12/1984 | United Kingdom . |

OTHER PUBLICATIONS

Coleman et al., "Applications of Therapeutic Ultrasound in Opthalmology", reprinted from Progress in Medical Ultrasound, vol. 2/1981, Amsterdam, Excerpta Medica, pp. 263-270.

*Primary Examiner*—Lee S. Cohen
*Attorney, Agent, or Firm*—William A. Drucker

[57] ABSTRACT

A hyperthermia treatment apparatus combining a generator of a focused ultrasonic beam comprising a main high frequency electric wave emitter and a main piezoelectric transducer whose active surface is focusing, with an echography device comprising an auxiliary high frequency electric pulse generator associated with an auxiliary piezoelectric transducer and means for causing the zone to be treated to be swept by the ultrasonic examination beam generated by said auxiliary transducer; and with switching and adjustment means for causing, during a main treatment and checking operating mode, emission of said focused beam by said main transducer energized by said main emitter during periodic time intervals separated by shorter time intervals during which the emission of the examination beam and the formation of echographic images are effected.

25 Claims, 3 Drawing Sheets

| | | |
|---|---|---|
| 3,735,755 | 5/1973 | Eggleton et al. . |
| 3,756,071 | 9/1973 | Dory . |
| 3,785,382 | 1/1974 | Schmidt-Kloiber et al. . |
| 3,942,531 | 3/1976 | Hoff et al. . |
| 3,974,682 | 8/1976 | Soldner et al. . |
| 4,005,258 | 1/1977 | Dory . |
| 4,046,149 | 9/1977 | Komiya . |
| 4,058,114 | 11/1977 | Soldner . |
| 4,070,905 | 1/1978 | Kossoff . |
| 4,163,394 | 8/1979 | Soldner . |
| 4,218,768 | 8/1980 | Hassler . |
| 4,235,111 | 11/1980 | Hassler . |
| 4,245,511 | 1/1981 | Soldner . |
| 4,274,421 | 6/1981 | Dory . |
| 4,281,661 | 8/1981 | Dory . |
| 4,287,770 | 9/1981 | Weyns . |
| 4,294,119 | 10/1981 | Soldner . |
| 4,311,147 | 1/1982 | Hausler . |
| 4,340,944 | 7/1982 | Dory . |
| 4,368,410 | 1/1983 | Hance et al. . |
| 4,373,395 | 2/1983 | Borburgh et al. . |
| 4,412,316 | 10/1983 | Diepers . |
| 4,434,341 | 2/1984 | Busby . |
| 4,458,533 | 7/1984 | Borburgh . |
| 4,462,092 | 7/1984 | Kawabuchi et al. . |
| 4,474,180 | 10/1984 | Angulo . |
| 4,478,083 | 10/1984 | Hassler et al. . |
| 4,484,569 | 11/1984 | Driller et al. . |
| 4,486,680 | 12/1984 | Bonnet et al. . |
| 4,536,673 | 8/1985 | Forster . |
| 4,545,385 | 10/1985 | Pirschel . |
| 4,564,980 | 1/1986 | Diepers . |
| 4,586,512 | 5/1986 | Do-huu et al. . |
| 4,618,796 | 10/1986 | Riedlinger . |
| 4,618,887 | 10/1986 | Birk . |
| 4,620,545 | 11/1986 | Shene et al. . |
| 4,639,904 | 1/1987 | Riedlinger . |
| 4,658,828 | 4/1987 | Dory ............................. 128/660.03 |
| 4,671,292 | 6/1987 | Matzak . |
| 4,721,106 | 1/1988 | Kurtze et al. . |

OTHER PUBLICATIONS

Ultrasonic Focusing Radiators, pp. 225–285, 306–307.

Berlinicke et al., "Uber Beeineflussung Von Gallensteinen Durch Ultraschall in Vitro", Klinitsche Wochenschrift, Dec. 28, 1950, p. 390.

Mulvaney, "Attempted Disintegration of Calculi by Ultrasonic Vibrations", The Journal of Urology, vol. 70, No. 5, Nov. 1953, pp. 704–707.

Coats, "Application of Ultrasonic Energy to Urinary and Biliary Calculi", The Journal of Urology, vol. 75, No. 5, May 1956, pp. 865–874.

Bergmann, "Der Ultraschall—und Siene Anwendung in Wissen Schaft und Technik", S. Hirzel Verlag, Stuttgart, 1954, pp. 126–137.

Friedland, "Present Status of Ultrasound in Medicine", The Journal of the American medical Association, vol. 163, No. 10, Mar. 1957, pp. 799–803.

Fry, "Precision High Intensity Focusing Ultrasonic Machines for Surgery", American Journal of Physical Medicine, vol. 37, No. 3, Jun. 1958, pp. 152–156.

Fry et al., "Ultrasonic Visualization of Soft Tissue Structure Based on Gradients in Absorption Characteristics", The Journal of the Acoustical Society of America, vol. 35, No. 11, Nov. 1963, pp. 1788–1790.

Guilgkett; "Stobspannungen und Stobstrome"(source unknown), pp. 2–22.

Gekhman et al., "The Effect of Supersonic Waves upon the Kidneys and the Urinary Tract", (Russian) 1963, pp. 17–21.

Tarnoczy, "Sound Focussing Lenses and Wave Guides", Ultrasonics, Jul.–Sep., 1965, pp. 115–127.

Lele, "Production of Deep Focal Lesions by Focused Ultrasound—Current Status", Ultrasonics, Apr. 1967, pp. 105–112.

Kurtze, "Uber die Bedingunguen fur das Auftreten von Kavitation in Flussig Keiten", (source unknown), pp. 1–47.

Rozenberg, "Sources of High Intensity Ultrasound", Plenum Press, New York, 1969, vol. 1, Chapter 4, pp. 288–307.

Fry, "Ultrasonic Visualization", Confinia Neurologica, vol. 32, pp. 38–52, 1970.

(List continued on next page.)

OTHER PUBLICATIONS rungsfreien Nierensteinzertrummerung an der Freigelegten Niere", Urologe A 18 (1979), pp. 289–293.

"Echographie Ultrasonore: Un Circuit CCD Pour Simplifier L'Electronique De Commande", Mesures Regulation Auromatisme—Fevrier 1980, pp. 25–27.

Chaussy, "Beruhrungsfreie Nierensteinzertrummerung Durch Extrakorporal Erzeugte, Fokussierte Stobwellen", Beitrage Zur Urologic, vol. 2, Karger, Basel, 1980, pp. 40–41, Translation of entire source included.

Chaussy et al., Extracorporeal Shock Wave Lithotripsy—New Aspects in the Treatment of Kidney Stone Disease, Karger, Basel, 1982.

Coleman et al., "Ultrasonically Accelerated resorption of Vitreous Membranes", American Journal of Opthalmology, 89:490–499, 1980.

Lizzy et al., "Experimental Treatment of Intra-ocular Carcinoma with High Intensity Focused Ultrasound", Paper No. 1305, Proceedings of the 25th Annual Meeting of the American Institute of Ultrasound in Medicine, Sep. 15–19, 1980, New Orleans, Lousiana.

Hausler and Stein, "Fokussierbare Unterwasserimpulsschallquellen", Acustica, vol. 49, No. 4, 1981, pp. 273–279.

Coleman et al., "Production of Alternate Filtration Paths for Treatment of Glaucoma with High Intensity Ultrasound", Paper No. 1303, AIUM/SDMS Annual Convention, San Francisco, California, Aug. 17–21, 1981.

Bulow et al., "Electrohydraulic Lithotripsy with Aspiration of the Fragments Under Vision—304 Consecutive Cases", The Journal of Urology, vol. 126, Oct. 1981, pp. 454–456.

Riedlinger et al., "Generation of High Energy Ultrasound Impulses with Focusing Piezoelectric Transducers", Fortschritte der Akustik, FASA/DAGA, '82, Gottingen, 1982, pp. 755–758.

Chaussy et al., "First Clinical Experience with Extracorporeally Induced Destruction of Kidney Stones by Shock Waves", The Journal of Urology, vol. 127, Mar. 1982, pp. 417–420.

Ziegler et al., "Erfahrungen mit Hochenergetischen Stobwellen Bei der Behandlung Von Nierensteinen", Results of High Intensity Shock Wave Treatment of Renal Calculi, Piezoelectric Ceramics, Ghent, Belgium, 1982.

Howards et al., "Current Status of Mechanical Lithotripsy", Transactions of the American Association of Genito-Urinary Surgeons, vol. 65, 1973, pp. 123–125.

Gavriiov et al., "Use of Focused Ultrasound to Accelerate the Maturing of a Cataract", Sov. Phys. Acoust., vol. 20, No. 3, Nov.–Dec. 1974, pp. 229–231.

Hausler, "Physikalische Grundlagen Der Instrumentellen Und Der Extrakorporalen Zerkleinerung Von Harnsteinen" (source unknown), p. 32.

Hausler et al., "Ultraschallverfahren Zur Ortung Von Nierensteinen" (source unknown), pp. 54–60.

Bittner, "Uber Die Moglichkeiten, Nierensteine Mit Hilfe Des Ultraschall-A-Verfahrens Nachzuweisen Und Zu Lokalisieren" (source unknown), pp. 61–69.

Bartels, "Zur Frage Der Nierenstein-Darstellung Mit Der B-Scan Sonographie" (source unknown), pp. 70–73.

Bartels, "Intraoperative Rontegenuntersuchungen Der Niere Mit Dem Renodorgerat" (source unknown), pp. 74–81.

Wells, "Biomedical Ultrasonics", Academic Press, London, 1977, pp. 494–495.

Ibid., pp. 208–213.

Ibid., pp. 511–594.

Coleman et al., "Therapeutic Ultrasound in the Production of Ocular Lesions", American Journal of Opthalmology, 86:185–192, 1978.

Fry, "Ultrasound: Its Applications in Medicine and Biology", Elsevier Scientific Publishing Company, Amsterdam, 1978, pp. 689–745.

Hausler et al., "Properties and Physiological Application of Focussed Fluid Shock Waves", ASA Meeting, Honolulu, Hawaii, Dec., 1978, pp. 2–12.

Petersen, "Piezoelektrische Aktuatoren", Feinwerktechrik E. Messtechnik, 86 (1978), pp. 304–308.

Raudsz, "Pschrometrische Bestimmung", Feinwerktechnik & Messtechnik 86 (1978). p. 303.

Konrad et al., "Fokussierte Stobwellen zur Beruh- (List continued on next page.)

OTHER PUBLICATIONS

Program of the 7th Annual Meeting, European Intrarenal Surgery Club, Ghent, Belgium, 1982.

Watanabe et al., "Micro-Explosion Cystolithotripsy", The Journal of Urology, vol. 129, Jan. 1983, pp. 23-28.

Hunt et al., "Ultrasound Transducers for Pulse-Echo Medical Imaging", IEEE Transactions on Biomedical Engineering, vol. BME-30, No. 8, Aug. 1983, pp. 453-481.

Chaussy et al., "Extracorporeal Shock Wave Lithotripsy (ESWL) for Treatment of Urolithiasis", Special Issue to Urology, vol. 23, No. 5, May 1984, pp. 59-66.

Elder et al., "Ultrasonic Lithotripsy of a Large Staghorn Calculus", The Journal of Urology, vol. 131, Jun. 1984, p. 1152-1154.

Hynynen et al., "A Clinical Hyperthermia Unit Utilizing an Array of Seven Focused Ultrasnoic Transducers", 1983, Ultrasonics Symposium, IEEE, pp. 815-921.

Chaussy et al., "Extrakorporale Stobwellenkithotripsie—Beginn einer Umstrukturierung in der Behandlung des Harnsteinleidens", Urologe A, vol. 23, 1984, pp. 25-29.

Chaussy et al., "Shock Wave Treatment for Stones in the Upper Urinary Tract", Urologic Clinics of North America, vol. 10, No. 4, Nov. 1983, pp. 743-750.

Brannen et al., "Ultrasonic Destruction of Kidney Stones", Original Clinical Articles, Mason Clinic, Seattle, Feb., 1984, vol. 140, No. 2, pp. 227-232.

Lizzy et al., "Thermal Model for Ultrasonic Treatment of Glaucoma", Ultrasound in Med & Biol., vol. 10, No. 3, 1984, pp. 289-298.

Wanner et al., "Problematik Einer Integrierten Ultraschallortung Im Versuchsmodell" Beruhrungsfreie Nierensteinzertrummerung, Symposium Biophysikalische Verfahren zur Diagnose und Therapie von Steinleiden der Harnwege, Meersburg, Jul. 10 and 11, 1987, pp. 235-240.

EXAMINING, LOCALIZING AND TREATMENT WITH ULTRASOUND

This is a division of Ser. No. 037,369, filed Apr. 13, 1987, abandoned, which is a division of Ser. No. 728,905, filed Apr. 30, 1985, which is U.S. Pat. No. 4,658,828, now U.S. Pat. No. Re. 33,590 of May 21, 1991 which is a continuation-in-part of Ser. No. 674,889, filed Nov. 26, 1984, now U.S. Pat. No. 4,617,931, now Re-Examination Certificate B1-4,617,931 of July 12, 1988.

BACKGROUND OF THE INVENTION

Conventional echography apparatus are obviously used for examining tumours inside the body by forming an image thereof on the screen of a cathode ray tube.

As is known, it is also possible to obtain destruction of the cells—in particular malignant cells—by subjecting them to a more or less extended temperature rise. The cells to be destroyed must for example be brought to about 45° C. in a well controlled way while avoiding reaching excessive temperatures which could cause serious burns around the lesion. The technical problem to be resolved consists then both in controlling the amount of energy and the localization thereof.

With the different prior processes (use of ultra-high frequencies, infrared radiation, and others) superficial tumours can be treated but deeper tissues cannot be reached.

The invention proposes applying ultra sounds to the examination and hyperthermia treatment and provides an apparatus which combines the three functions of localizing the zone to be treated, of treating by raising the temperature in a well controlled way in a well defined restricted region within this zone and simultaneously checking the results of the treatment.

SUMMARY OF THE INVENTION

The hyperthermia treatment apparatus of the invention combines a generator of a focused ultra sonic beam comprising a main high frequency electric wave emitter and a main piezoelectric transducer whose active surface is focusing, with an echography device comprising an auxiliary high frequency electric pulse generator associated with an auxiliary piezoelectric transducer and with means for causing the zone to be treated to be swept by the ultrasonic examination beam being generated by the auxiliary transducer; and with switching and adjusting means for causing, during main treatment and checking operation, the emission of said focused beam by the main transducer energized by the main emitter during periodic time intervals separated by shorter time intervals during which the emission of the examination beam and the formation of echographic images are carried out.

The apparatus advantageously comprises a first auxiliary locating operation mode during which only the periodic emission of the examination beam by the auxiliary transducer is effected and preferably a second auxiliary operating mode for checking the focal region, during which only the periodic emission of the focused beam is effected, but the main emitter is synchronized by the synchronization circuit of the auxiliary generator for echographic operation, the time intervals which separate the successive emission periods during the two auxiliary operation modes being substantially smaller than the intervals which separate the periods of emission of the focused beam during the main mode.

It follows from the foregoing that, during the auxiliary operating modes for obtaining accurate adjustments, the quality of the echographic image, either of the zone to be treated (locating mode) or of the focal region (mode for checking the restricted region), will be substantially better than during the treatment mode, during which the successive images of the zone to be treated will follow each other for example at intervals of the order of a second, which however allow the position of the focal region to be checked satisfactorily during treatment.

In a preferred embodiment, the auxiliary transducer is fixed to the spherical surface of the main transducer and thus, during movement of this latter for bringing the focal spot into successive restricted regions of the tumour, the auxiliary transducer will at all times supply an image of the treated region and of the zone which surrounds it, thus allowing a permanent check of the treatment to be effected easily and accurately.

BRIEF DESCRIPTION OF THE DRAWINGS

Other features and advantages of the invention will be clear from the following description.

In the accompanying drawings.

DESCRIPTION OF THE PREFERRED EMBODIMENT

Figure 2:
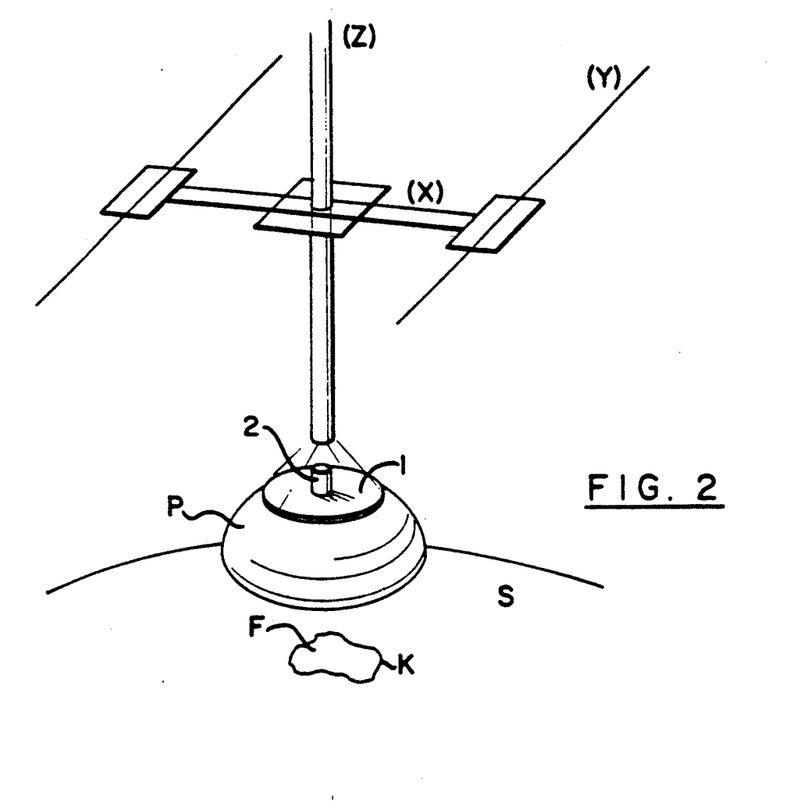
FIG. 2 shows schematically in perspective the main transducer and its mobile support device.

In FIG. 2 is shown a main transducer 1 in the form of a spherical skull cap supported by a mount which allows it to move along three orthogonal axes X, Y and Z. This mount has been shown schematically, its construction being within the scope of a man skilled in the art. Along the axis of the spherical skull cap is disposed an auxiliary transducer 2 of a generally cylindrical shape which passes through skull cap 1 and is fixed thereto. A pocket of water P is placed between the skull cap 1 and the surface S of the body of the patient, who is assumed lying flat on a horizontal plane.

The skull cap 1 has for example a diameter of 200 to 300 mm and is formed from a large number (300 or 400) of piezoelectric elements 10, 11, etc. . . . (FIG. 1) isolated from each other and juxtaposed so as to form a mosaic. These elements are metallized on both faces, one of the metallizations being connected to ground and the other to connections for energization by a main emitter 3.

Figure 3:
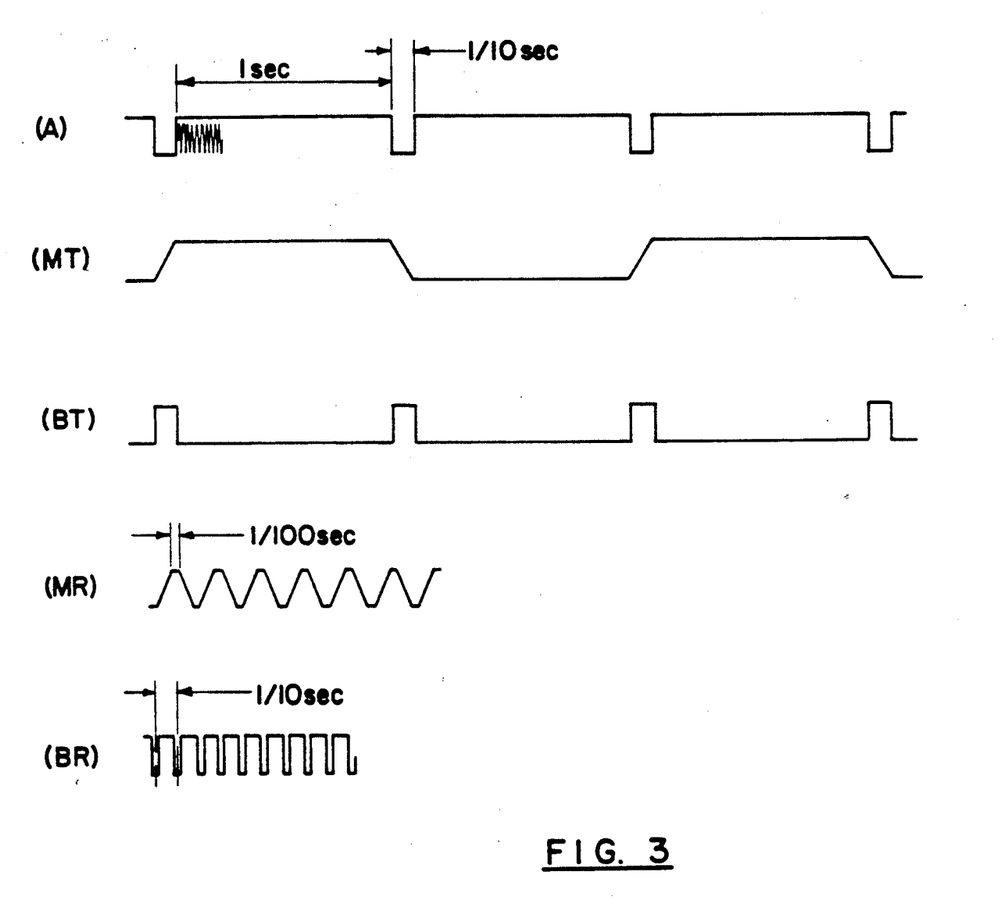
FIG. 3 shows the wave forms at different points of the circuits of the apparatus.

This latter delivers an electric signal A (FIG. 3) formed of high frequency wave trains (500 KHz for example) of a relatively low peak power (about 10 or a 100 watts for example), but of a relatively long duration (for example of the order of a second) separated by time intervals of the order of 1/10 second, the time required for the echography device to form an image. It is then a question of operating conditions using substantially continuous emission for the treatment. Such operating conditions may be obtained by means of emitters using power transistors. Preferably, the elements of transducer 1 will be divided up into groups each energized by a separate emitter (rectangle 4 symbolizing the assembly of these emitters), the elements of each group being spaced apart in the same circular zone of the spherical surface. By adjusting the relative phases of the emissions, it is possible to modify the energy distribution in the focusing region of the ultra sonic beam.

An input 31 to emitter 3 symbolizes an adjustment of the emitted power and an input 32 symbolizes an adjustment of the wave train duration. The focal spot formed in the center F of the sphere may, with this technique, be very small (diameter of 2 or 3 mm for example) and have a position which is strictly fixed for a given position of the transducer.

Figure 1:
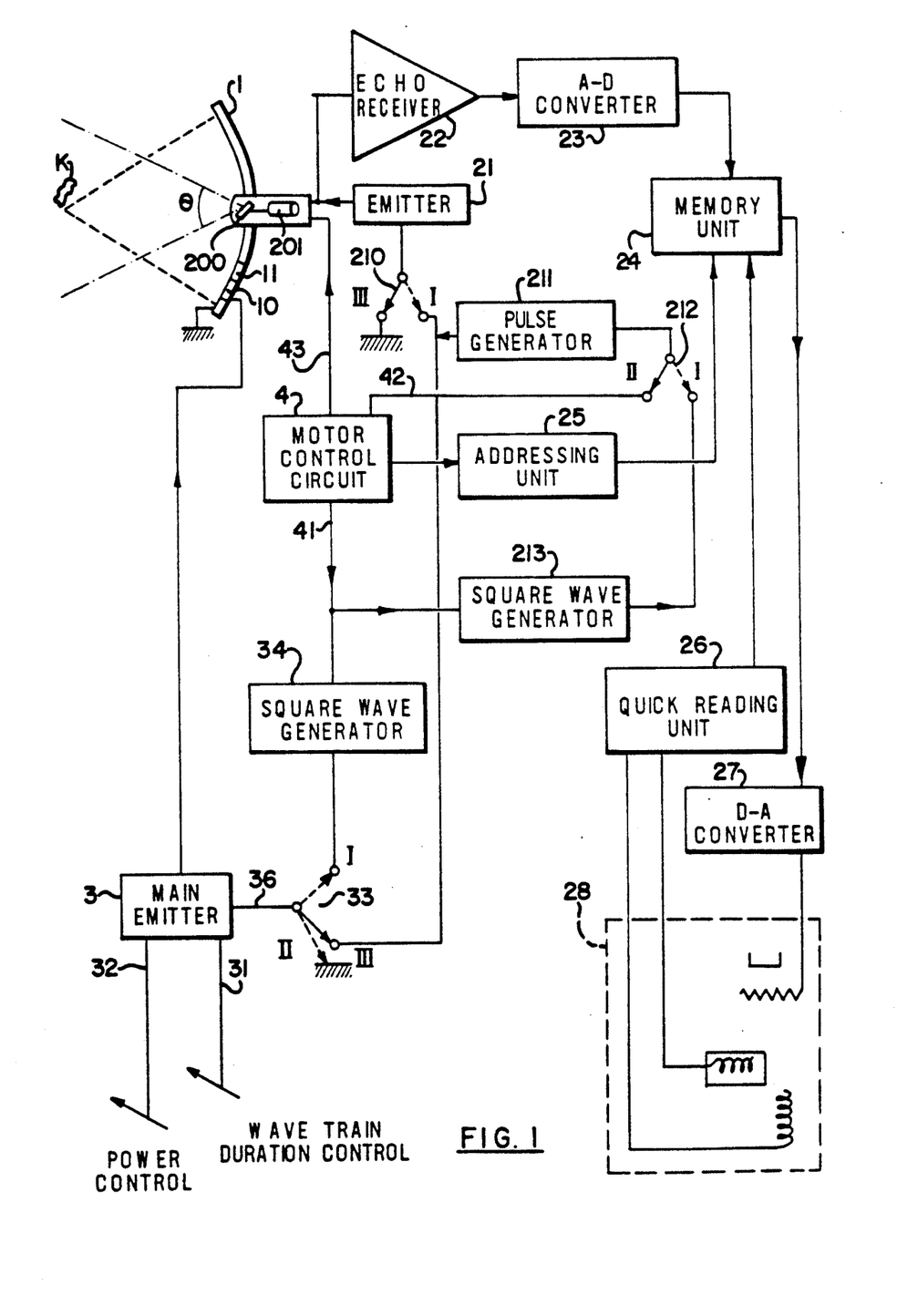
FIG. 1 is the general diagram of a hyperthermia apparatus according to a preferred embodiment of the invention.

In FIG. 1 it can be seen that the auxiliary transducer 2 is itself connected both to a high frequency electric pulse emitter 21 and to a reception amplifier 22 followed by an analog-digital converter 23, itself followed by a memory 24. Emitter 21 is synchronized by a pulse generator 211 which delivers 256 pulses during each of the successive time intervals of 1/10 second. To each of these time intervals corresponds a complete sweep of a given angular sector θ (FIG. 1) by the beam emitted by transducer 2 so the formation, in the sweep plane, of an image of the zone observed by the echography device.

Transducer 2 is advantageously of the type described in French patent applications number 80 16717 filed on the 29 July 1980 for: "A sectorial sweep echography probe comprising two coupling liquids", and N° 80 16718 filed on the 29 July 1980 for: "Mechanical sectorial sweep echography probe", that is to say that it comprises an oscillating piezoelectric element 200 controlled by a motor 201, itself controlled by an electronic circuit which is shown symbolically by a rectangle 4. This electronic circuit provides control signals for the motor 201 housed inside the case of the transducer 2 and is adapted so that a complete oscillation of the motor corresponds to the above defined duration for forming an image (1/10 sec.).

In a first operating mode (treatment and checking) switch 210 is in position I as well as switches 212 and 33.

Figure 4:
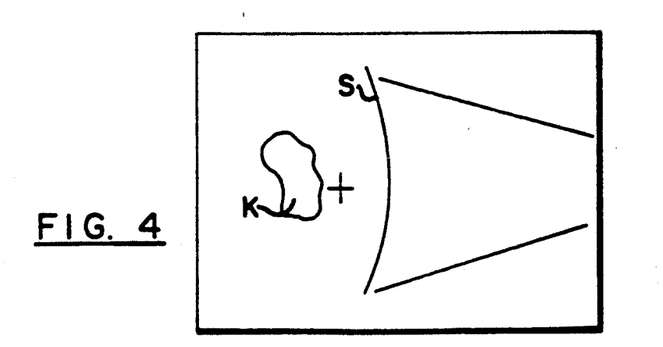
FIG. 4 illustrates the image obtained on the display screen which the apparatus comprises.

In position I of switches 33 and 212, generator 211 is synchronized by a first output 41 of circuit 4, and this latter is then adjusted, by means not shown, for generating at its output 43 connected to motor 201 signals having the wave form (MT) shown in FIG. 4. An image is swept then in 1/10 sec. and is followed by a time interval of 1 sec. during which the oscillating element 200 remains immobile, so that transducer 2 receives no echos.

During the intervals between the sweep periods, a circuit 34 generates square waves of 1 sec. which serve for synchronizing emitter 3 whereas, during the sweep periods, a circuit 213 generates square waves of 1/10 sec. which serve for synchronizing the generator 211.

Thus, in this operating mode, transducer 1 generates an ultra-sonic beam under substantially continuous operating conditions whereas the echography device forms an image every second in the intervals between the wave trains. At (BT) has been shown the wave forms of the signals then emitted by generator 211.

In a second operating mode (locating) with switch 210 in position I, switch 33 is in position II, so that emitter 3 is not synchronized and the focused ultrasonic beam is not emitted. Switch 212 is also in position II so that generator 211 is synchronized by a second output 42 of circuit 4 and this latter is adjusted so as to generate at its output 43 signals having the wave forms (MR) shown in FIG. 3. The 1/10 sec. sweeps are then separated by time intervals of 1/100 sec. only and the images are formed from echos coming from the reflection of the pulses generated by transducer 2. Generator 211 delivers the signals (BR).

In a third operating mode (checking the focal region), switch 210 is in position III, so that the emitter 21 and transducer 2 do not emit. Switch 212 is again in position II so that generator 211 is synchronized by the output 42 of circuit 4 and this latter is adjusted as in the second operating mode so that the 1/10 sec. sweeps are again separated by intervals of 1/100 sec. Switch 33 is in position III and consequently emitter 3 is now synchronized by the generator 211 which then delivers the signals (BR).

In this third operating mode, the echographic device is therefore formed by emitter 3, transducer 1 operating for emission and transducer 2 operating for reception. The result is that an image of the zone of concentration in the focal region of the energy emitted by the transducer 1 is obtained.

The echographic signals received at 22 in the first or third operating modes are, after analog-digital conversion at 23, stored line by line in memory 24, a writing addressing device 25, controlled by circuit 4, causing the respective deflection angles of the beam emitted and/or received by transducer 2 to correspond with the respective lines of the memory. A device 26 for rapid reading of the memory energizes the X and Y deflection coils of a cathode ray tube 28, so the brightness control electrode receives the corresponding contents from memory 24, transformed into an analog signal by a digital-analog converter 27.

The practical construction of all the circuits described and shown is within the scope of a man skilled in the art. The control circuit 4 may for example comprise a one shot multivibrator delivering square waves of a duration adjustable to 1/100 s or 1 s depending on the operating mode and circuits for generating increasing and decreasing voltages of a 1/10 s duration, triggered off by said square waves.

The apparatus which has just been described operates as follows:

In the locating operating mode, the operator searches for and localizes the zone to be treated. The display device is adapted, in a way known per se, so as to materialize on the screen of the cathode ray tube (for example by means of a cross) the theoretical position of the focal spot in the sectional plane shown, which plane passes through the axis of symmetry of transducer 1. (It is a question of B type echography). The operator begins by moving transducer 1 along X, until the tumour appears clearly on the screen, then he moves it along Y and Z, until the cross coincides with the central region of the image of the tumour (K, FIG. 4). At this moment, the switches may be placed in position for checking the focal region: only this latter is then made visible on the screen, with a luminosity proportional to the corresponding energy concentration. Thus a representation is obtained of what the distribution of the energy of the treatment wave will be, which allows the adjustments to be checked and perfected.

During treatment, the apparatus only supplies one image per second, but this rate is sufficient for substantially permanently checking the position of the focal spot.

It is clear that the apparatus described allows the evolution of the tumour to be checked after each treatment sequence. It is evident that different modifications may be made thereto and even according to other embodiments, without departing from the scope and spirit of the invention.

What is claimed is:

1. A device for extracorporeal wave treatment of a target within a living body comprising:
   (i) electric wave generator means and transducer means, said electric wave generator means connected to said transducer means to cause said transducer means to produce treatment waves;
   (ii) a water containing enclosure and means adapted to focus the treatment waves through said enclosure at a focal spot located out of said water containing enclosure;
   (iii) means connecting said generator means to said transducer means;
   (iv) image forming means sweeping an ultrasound scanning wave through said water between said focal spot and said means adapted to focus the treatment waves, said image forming means displaying an image of said target with a visual indication of the position of said focal spot; and
   (v) means displacing said transducer means and the image forming means to bring said image and said indication into coincidence.

2. The apparatus of claim 1 wherein said transducer means effects hyperthermia.

3. The apparatus of claim 1 wherein said treatment waves are ultrasonic treatment waves.

4. A method for operating an extracorporeal treatment device which treats a target within a living body comprising:
   (i) generating treatment waves;
   (ii) focusing said treatment waves through a water containing enclosure at a focal spot located outside of said enclosure with focus means from a treatment wave transducer;
   (iii) displaying an image of said target by sweeping ultrasound scanning waves from a scanning transducer which is displaced with the treatment wave transducer through said water between the focal spot and the said treatment focus means together with a visual indication of the position of said focal spot; and
   (iv) displacing said treatment wave transducer to bring said image and said indication into coincidence.

5. The method of claim 4 wherein said treatment waves effect hyperthermia.

6. The method of claim 4 wherein said treatment waves are ultrasonic waves.

7. A method for operating an extracorporeal treatment device which treats a target within a living body comprising:
   (i) generating treatment waves;
   (ii) focusing said treatment waves through a water containing enclosure at a focal spot located outside of said enclosure from a treatment wave transducer;
   (iii) displaying an image of said target together with a visual indication of the position of said focal spot;
   (iv) generating said image by sweeping ultrasound scanning waves from a scanning transducer which is displaced with the treatment wave transducer across said target; and
   (v) displacing said treatment wave transducer to bring said image and said indication into coincidence.

8. The method of claim 7 wherein said treatment waves effect hyperthermia.

9. The method of claim 7 wherein said treatment waves are ultrasonic waves.

10. A method for examining, localizing and treating a zone within a body comprising the steps of:
    (a) generating a first treatment beam from a first transducer focused on said zone;
    (b) successively discharging the first beam to treat said zone with said first beam;
    (c) generating a second imaging scanning beam from a separate second transducer;
    (d) effecting a scanning of said zone only with the second beam by sweeping said second beam across said zone to effect imaging of said zone;
    (e) receiving the echoes formed through reflection of the second beam on reflecting surfaces of said zone and converting said echoes into electrical signals; and displaying said signals during treatment at least between successive treatment discharges as real time images.

11. The method of claim 10 wherein said treatment beam effects hyperthermia.

12. The method of claim 10 wherein said treatment beam is an ultrasonic beam.

13. A method for treating a zone, having reflecting surfaces for ultrasonic waves and located within a body, by an interrupted beam of treatment vibrations generated from a treatment transducer and converging at a focus, said method comprising the steps of:
    (a) locating said zone by generating an echographic ultrasonic beam from an echographic transducer and effecting periodic sweeps across said focus; real time scanning said zone with said echographic beam, whereby echoes are formed through reflection of said echographic beam on said reflecting surfaces; receiving echoes from said surfaces; converting the received echoes into electric signals and forming from said signals two dimensional real time images of said zone through at least one plane;
    (b) treating said zone by generating treatment beam discharges from said treatment transducer focused on said zone; and
    (c) scanning and sweeping said zone at least between treatment discharges with said echographic beam to produce real time images of treatment progress.

14. The method of claim 13 wherein said tratment beam discharges effect hyperthermia.

15. The method of claim 13 wherein said treatment beam discharges are focussed in an ultrasonic beam.

16. A method for altering a zone within a body, comprising the steps of:
    (a) locating said zone by reflected ultrasonic scanning waves from a first transducer;
    (b) focusing on said zone and applying to said zone a beam from a second transducer of treatment wave discharges separated by time intervals to alter said zone, said beam converging along a path at a focal spot; and
    (c) generating ultrasonic scanning waves from said first transducer, real time sweeping said zone by transmitting to and reflecting from said zone an ultrasonic wave beam across said focal spot to form and display real time images from reflected ultrasound waves at least during said intervals and viewing said zone on-line during said treatment.

17. The method of claim 16 wherein said treatment beam effects hyperthermia.

18. The method of claim 16 wherein said treatment beam discharges are focussed in an ultrasonic beam.

19. A method for noninvasive treatment of a zone within a body of a patient, comprising the steps of:
   (a) providing a focusing surface having a fixed focal point at a distance from said surface; and a first ultrasonic scanning transducer having an axis passing between said focal point and said surface, said scanning transducer being coupled to said surface and radiating an ultrasonic signal beam;
   (b) positioning said surface to locate said focal point of said surface at said zone;
   (c) ultrasonically locating said zone with said scanning transducer by sweeping said signal beam across an angular sector including said zone;
   (d) generating from a second treatment transducer a vibration treatment wave focused by said surface upon said zone; and
   (e) acoustically coupling said treatment wave through a portion of said body whereby treatment wave energy is concentrated at said zone.

20. The method of claim 19 wherein said treatment wave is an ultrasonic treatment wave.

21. The method of claim 19 wherein said treatment wave is an ultrasonic wave.

22. A method for locating and altering a zone within a body, comprising the steps of:
   (a) locating a zone by ultrasonic scanning signals from a first transducer;
   (b) focusing on said zone and applying to said zone from a second transducer coupled to said first transducer a beam of treatment wave discharges to alter said zone; and
   (c) scanning said zone by sweeping an ultrasound beam across said zone through an ultrasound coupling to said body containing said zone and viewing said zone on-line during treatment.

23. The method of claim 22 wherein said treatment wave effects hyperthermia.

24. The method of claim 22 wherein said treatment wave discharges are focussed in an ultrasonic wave.

25. A method for treatment of a zone within a body of a patient, comprising the steps of:
   (a) providing a focusing surface having a focal point at a distance from said surface; and a first ultrasonic scanning transducer having an axis between said focal point and said surface, said scanning transducer being coupled to said surface and radiating an ultrasonic signal beam;
   (b) locating said zone by sweeping said signal beam across an angular sector including said zone to provide visual display information from said zone;
   (c) positioning said surface to locate said focal point at said zone which comprises the steps in any order of:
   (d) moving said surface in a first direction in response to the visual display information of said zone;
   (e) moving said surface in a second direction in response to said visual display information from said zone;
   (f) moving said surface in a third direction in response to said visual display information from said zone wherein movement in said third direction moves said surface in a direction essentially perpendicular to said body and wherein said third direction is perpendicular to both said first direction and said second direction; and
   (g) bringing said display from said zone into coincidence with a visual indicator of the focal point position.

* * * * *